United States Patent
Francischelli et al.

(10) Patent No.: US 6,488,680 B1
(45) Date of Patent: Dec. 3, 2002

(54) VARIABLE LENGTH ELECTRODES FOR DELIVERY OF IRRIGATED ABLATION

(75) Inventors: David E. Francischelli, Anoka, MN (US); Richard H. Comben, St. Paul, MN (US); Michael F. Hoey, Shoreview, MN (US); Rahul Mehra, Stillwater, MN (US); Jon M. Ocel, New Birghton, MN (US); Robert Pearson, Woodbury, MN (US); Paul V. Trescony, Champlin, MN (US); Scott E. Jahns, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/558,975

(22) Filed: Apr. 27, 2000

(51) Int. Cl.⁷ .............................................. A61B 18/18
(52) U.S. Cl. .............................. 606/41; 606/47; 606/48; 606/51
(58) Field of Search ................................ 607/101, 102; 606/41, 47, 48, 49, 50–52

(56) References Cited

U.S. PATENT DOCUMENTS

| | | | |
|---|---|---|---|
| 623,022 A | * 4/1899 | Johnson | 606/41 |
| 4,567,890 A | 2/1986 | Ohta et al. | |
| 5,383,876 A | 1/1995 | Nardella | 606/49 |
| 5,417,709 A | 5/1995 | Slater | 606/205 |
| 5,584,872 A | * 12/1996 | La Fontaine et al. | 607/116 |
| 5,609,151 A | 3/1997 | Mulier et al. | 128/642 |
| 5,647,871 A | 7/1997 | Levine et al. | 606/45 |
| 5,722,403 A | 3/1998 | McGee et al. | 128/642 |
| 5,725,524 A | 3/1998 | Mulier et al. | 606/41 |
| 5,807,395 A | 9/1998 | Mulier et al. | 606/41 |
| 5,871,469 A | 2/1999 | Eggers et al. | 604/114 |
| 5,897,553 A | 4/1999 | Mulier et al. | 606/41 |
| 5,906,613 A | 5/1999 | Mulier et al. | 606/41 |
| 5,913,854 A | 6/1999 | Maguire et al. | |
| 5,919,188 A | 7/1999 | Shearon et al. | |
| 5,925,038 A | * 7/1999 | Panesca et al. | 606/41 |
| 5,944,715 A | 8/1999 | Goble et al. | 606/41 |
| 5,951,546 A | 9/1999 | Lorentzen | 606/41 |
| 5,961,514 A | 10/1999 | Long et al. | 606/41 |
| 6,004,319 A | 12/1999 | Goble et al. | 606/48 |
| 6,010,500 A | * 1/2000 | Sherman et al. | 606/41 |
| 6,013,076 A | 1/2000 | Goble et al. | 606/41 |
| 6,015,406 A | 1/2000 | Goble et al. | 606/41 |
| 6,015,407 A | 1/2000 | Rieb et al. | 606/41 |
| 6,017,338 A | 1/2000 | Brucker et al. | 606/41 |
| 6,027,501 A | 2/2000 | Goble et al. | 606/41 |
| 6,032,077 A | 2/2000 | Pomeranz | 607/101 |
| 6,063,081 A | 5/2000 | Mulier et al. | 606/45 |
| 6,068,653 A | * 5/2000 | La Fontaine | 607/116 |
| 6,086,585 A | 7/2000 | Hovda et al. | 606/45 |
| 6,086,586 A | 7/2000 | Hooven | 606/50 |
| 6,090,106 A | 7/2000 | Goble et al. | 606/41 |
| 6,096,037 A | * 8/2000 | Mulier et al. | 606/49 |
| 6,117,132 A | 9/2000 | Long et al. | 606/41 |
| 6,119,041 A | * 9/2000 | Pomeranz et al. | 607/101 |
| 6,120,501 A | 9/2000 | Long et al. | 606/48 |
| 6,149,620 A | 11/2000 | Baker et al. | 604/22 |
| 6,162,220 A | 12/2000 | Nezhat | 606/48 |
| 6,168,594 B1 | * 1/2001 | La Fontaine et al. | 606/41 |
| 6,183,469 B1 | 2/2001 | Thapliyal et al. | 606/41 |
| 6,228,082 B1 | 5/2001 | Baker et al. | 606/49 |

(List continued on next page.)

Primary Examiner—Linda C. M. Dvorak
Assistant Examiner—David M. Ruddy
(74) Attorney, Agent, or Firm—Thomas G. Berry; Daniel W. Latham

(57) ABSTRACT

A device for ablating tissue is provided. The device comprises a conductive element with a channel for irrigating fluid formed therein, which is in contact with a non-conductive microporous interface. All or a portion of the interface may be removable. When the interface is removed, a portion of the conductive element is exposed for use in ablating tissue. Methods of using the device and of removing the interface are also provided.

41 Claims, 12 Drawing Sheets

U.S. PATENT DOCUMENTS

| | | |
|---|---|---|
| 6,238,391 B1 | 5/2001 | Olsen et al. .................. 606/41 |
| 6,238,393 B1 | 5/2001 | Mulier et al. ................. 606/41 |
| 6,241,666 B1 | 6/2001 | Pomeranz et al. .......... 600/381 |
| 6,254,600 B1 | 7/2001 | Willink et al. ............... 606/41 |
| 6,264,650 B1 | 7/2001 | Hovda et al. ................. 606/32 |
| 6,264,654 B1 * | 7/2001 | Swartz et al. ................ 606/45 |
| 6,277,112 B1 | 8/2001 | Underwood et al. .......... 606/32 |
| 6,277,114 B1 | 8/2001 | Bullivant et al. ............. 606/41 |
| 6,277,115 B1 | 8/2001 | Saadat ......................... 606/41 |
| 6,283,961 B1 | 9/2001 | Underwood et al. .......... 606/41 |
| 6,305,378 B1 * | 10/2001 | Lesh ............................ 606/41 |

* cited by examiner

VARIABLE LENGTH ELECTRODES FOR DELIVERY OF IRRIGATED ABLATION

FIELD OF THE INVENTION

This invention relates to ablation devices that are used to create lesions in tissue. More particularly, this invention relates to conductive elements for use in such devices which vary in length and which incorporate improved methods of irrigation delivery.

BACKGROUND OF THE INVENTION

The action of the heart is known to depend on electrical signals within the heart tissue. Occasionally, these electrical signals do not function properly. The maze procedure is a surgical operation for patients with chronic atrial fibrillation that is resistant to medical treatment. In this procedure, incisions are created in the right and left atria to produce an orderly passage of the electrical impulse from the SA node to the atrioventricular node. Blind passageways are also created to suppress reentry cycles. Currently, the lesions may still be created using a traditional cut and sew technique. The scar tissue resulting from the procedure results in a non-conductive lesion.

Ablation of cardiac conduction pathways in the region of tissue where the signals are malfunctioning is now being used to replace the surgical incisions. Ablation is also used therapeutically with other organ tissue, such as the liver, prostate and uterus. Ablation of organic tissue is also used in several surgical procedures, for both diagnosis and therapy.

In one type of procedure, one or more electrodes at the tip of an electrophysiology ablation device allow the physician to measure electrical signals along the surface of the heart (mapping). When necessary, in another type of procedure, the physician can also ablate certain tissues using, typically, radio frequency (RF) energy conducted to one or more ablation electrodes. During tissue ablation, energy is used to create lesions in the tissue for different purposes. High levels of energy are used to cut and remove tissue (electrosurgery). Lower levels of energy are used to cause cell damage but leave the structure intact so that electrical pathways are blocked within the tissue.

A variety of devices, such as catheters, are used to ablate tissue. Typically, such devices include a conductive tip, which serves as one electrode in an electrical circuit. The electrical circuit is completed via a grounding electrode that may also be on the device or may be coupled to the patient. By controlling the level of energy transmitted to the electrode, the surgeon is able to control the amount of heat generated for the purposes described above.

Irrigation of the ablation site cools the electrode. Irrigated ablation is also known to create deeper lesions that are more likely to be transmural. Transmurality is achieved when the full thickness of the target tissue is ablated.

During ablation, irrigation of the ablation site helps to cool the ablation electrodes, thereby reducing overheating in the vicinity of the electrodes. Undesirable consequences of overheating include the excessive coagulation of blood and the unintended destruction of healthy tissue adjacent the ablation site. The efficient cooling of the linear ablation electrode permits longer lesions to be created by permitting higher ablation energy without resulting in excessive electrode heating.

Typically, delivery of irrigation to the site is accomplished using a separate irrigation source which may pump into the ablation device or which may pump directly to the target tissue site. This requires a separate device that may not deliver irrigation as site-specifically as desired.

Furthermore, there is relatively high hydraulic impedance to saline flow at the distal end (towards ablation site) of a typical ablation device. In comparison, the hydraulic impedance to flow is lower at the proximal end (towards user) of the device. This sometimes results in more irrigation fluid being distributed at the proximal end than at the distal end.

Additionally, there may also be difficulties with electrical impedance to saline flow in a typical ablation device. This may be particularly true in a hemostat-type ablation device. In such a device, the target tissue is positioned between the two jaws of the hemostat, both of which carry ablation electrodes. If the tissue is shorter than the length of the hemostat jaws, a saline bridge may form between the hemostat jaws due to the surface tension of the fluid. This saline bridge is a low electrical impedance pathway. Electrical flow may, therefore, occur preferentially towards the bridge and yield unreliable ablation.

Irrigation fluid may also not be evenly distributed along a single electrode because of the impedance factors described above. Uneven distribution of fluid may result in an uneven lesion. In some cases, the tissue may not receive any irrigation in some areas. The electrode may contact the surface of the target tissue in these unirrigated areas, causing sticking or even charring.

Additionally, longer electrodes are sometimes desired to create longer lesions. These electrodes have a larger pressure drop along their length. This results in greater fluid flow from the proximal end than the distal end and thus irrigation is unevenly distributed which may result in sticking of the ablated tissue to the electrode. Currently an electrode of a given length is needed to create a lesion of a given length. If a lesion of a different length is desired, a new electrode must be used.

It would be desirable therefore to provide a means to control and vary irrigation.

It would further be desirable to facilitate control of lesion length.

It would further be desirable to provide a means for evenly irrigating an ablation electrode and concomitant target tissue site.

It would further be desirable to provide a means for evenly irrigating ablation electrodes of variable length.

It would further be desirable to provide a device in which irrigation capabilities and ablation capabilities are integrated.

SUMMARY OF THE INVENTION

One aspect of the present invention provides a device for ablating organic tissue. The device includes a conductive element, a fluid component in communication with the conductive element and a non-conductive interface positioned adjacent the tissue to allow the fluid to pass through the interface and contact the tissue. The conductive element may be, for example, a metallic coil with a lumen, a spring with a lumen or a wire. The diameter of the conductive element may be greater than the diameter of the interface. The conductive element and the interface may be the same. The interface may be microporous. The interface may also be of a variable length and a portion of the interface may be removable. The interface may be perforated, may comprise openings that are slidably or rotatably opened. The interface may be non-conductive or conductive. The interface may lie between the conductive element and the tissue surface. The interface may encircle the conductive element and the fluid component. The interface may be a rigid structure, a fluid saturated gel, or a microporous section of the fluid component. The interface and the fluid component may be the same. The fluid component may be a non-porous coating. The device may also include means for flowing the fluid component through the interface, such as an infusion pump.

Another aspect of the invention provides a device for creating ablations of variable length, comprising a conductive element having a channel formed therein, the channel operatively adapted to receive irrigating fluid; and a removable non-conductive interface in communication with the conductive element. The device may include a support element in communication with the conductive element. The support element may be a slotted tube. The conductive element may be a slotted tube.

Another aspect of the invention provides a device for creating ablations of variable length, comprising a non-porous tube operatively adapted to receive irrigating fluid therein, a conductive element in communication with the tube and a removable non-conductive interface in communication with the conductive element. The non-conductive interface may be a portion of the non-porous tube. The non-conductive interface may be micro-porous. The non-conductive interface may be rigid.

Another aspect of the present invention provides a device for creating ablations of variable length, comprising a non-porous tube operatively adapted to receive a hydrogel, a conductive element in communication with the tube and a removable non-conductive interface in communication with the conductive element. The non-porous tube may be slotted.

Another aspect of the present invention provides a method of ablating organic tissue. The method includes providing a conductive element having a channel formed therein, the channel operatively adapted to receive irrigating fluid; and a removable non-conductive interface in communication with the conductive element. The method also includes removing a portion of the interface to expose a portion of the conductive element and ablating the tissue with the exposed portion of the conductive element. The interface may be perforated. The interface may be disposable. The interface may be reusable. The interface may also be a removable tip.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
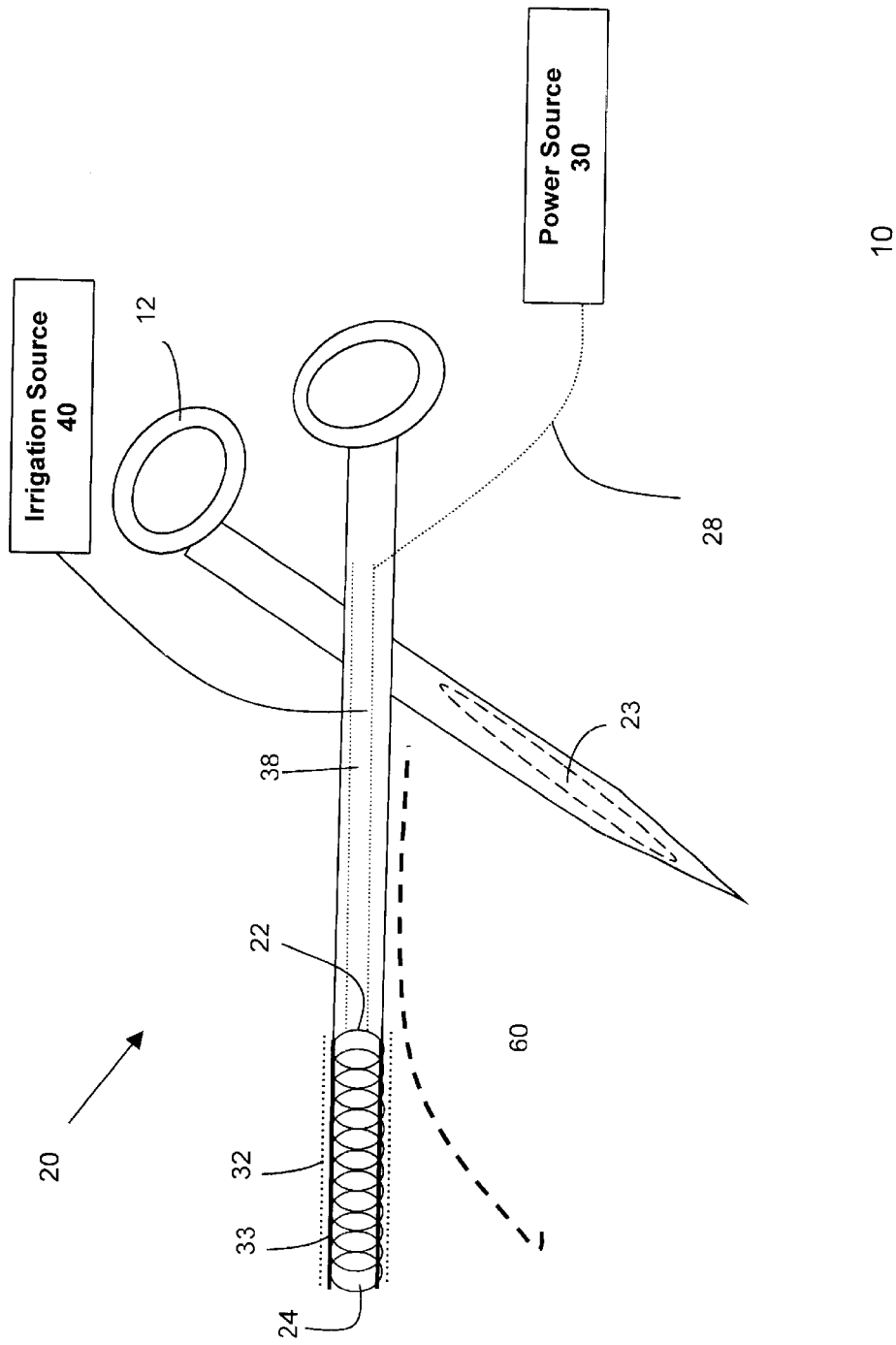
FIG. 1 is a schematic view of a system for ablating tissue in accordance with the present invention.

FIG. 1 shows a schematic view of one embodiment of system 10 for ablating tissue in accordance with the present invention. Typically the tissue to be ablated will be located within the body cavity, such as the endocardial or epicardial tissue of the heart. Other body organ tissue, such as the liver, can also be ablated using the present invention. System 10 may include an ablation device 20 that comprises at least one conductive element 22, such as an electrode, and a connection 28 to a power source 30. System 10 also may include a conduit 38 to an irrigation source 40 that provides irrigation fluid to the ablation site. System 10 may also include an insulating material 32 that may insulate conductive element 22. Insulating material 32 may also direct delivery of energy and/or irrigation along conductive element 22. System 10 may also include a support member 33 that may provide structural integrity to conductive element 22. System 10 may also include an indifferent electrode 23 which may serve as the return plate for energy transmitted through electrode 22. Electrode 23 may also be covered by insulating material and supported by a support member.

Ablation device 20 may be any suitable ablation tool such as, for example, a catheter, an electrocautery device, an electrosurgical device, a suction-assisted ablation tool, an ablation pod, an ablation paddle, an ablation hemostat or an ablation wire. Ablation device 20 and its components are preferably made of a biocompatible material such as stainless steel, biocompatible epoxy or biocompatible plastic. Preferably, a biocompatible material prompts little allergenic response from the patient's body and is resistant to corrosion from being placed within the patient's body. Furthermore, the biocompatible material preferably does not cause any additional stress to the patient's body, for example, it does not scrape detrimentally against any elements within the surgical cavity.

Preferably, ablation device 20 may be permanently or removably attached to a maneuvering apparatus for manipulating device 20 onto a tissue surface. For example, ablation device 20 may be attached to hemostat handles 12 such as shown in FIG. 1. Ablation device 20 may also be located on one or more of the hemostat jaws 32. Ablation device 20 may also be used in conjunction with a traditional catheter, for example, in a closed heart ablation procedure. Ablation device 20 may also be maneuvered with a leash or pull-wire assembly. Ablation device may also be positioned on a pen-like maneuvering apparatus such as the Cardioblate pen available from Medtronic, Inc. Alternatively any appropriate flexible or rigid handle could be used as a maneuvering apparatus. Alternatively, any appropriate endoscopic or thoroscopic-maneuvering apparatus may also be used with device 20.

Device 20 also preferably includes a connection 28 suitable for conducting energy to device 20, particularly to conductive element 22 from a power source.

The conductive element 22 of ablation device 20 is preferably an electrode. This electrode 22 may be positioned in any suitable place on device 20. Preferably electrode 22 is placed near an end of the device 20, away from the user, to be more easily manipulated against the tissue 60 to be ablated.

System 10 may also include an indifferent electrode 23 which may serve as the return plate for energy transmitted through electrode 22.

Electrode 23 may be placed elsewhere on the patient's body than the ablation site. For example, electrode 23 may be placed on the patient's back or thigh. Electrode 23 may also serve as a second ablation electrode in a bipolar arrangement. The two electrodes 22, 23 may be arranged on the jaws of a hemostat-like tool such as shown in FIG. 1. Electrodes 22, 23 may be arranged in other orientations to each other, such as, for example, parallel to each other on a surface.

As ablation occurs, it is sometimes desirable to irrigate the ablation site with irrigation fluid, which may be, for example, any suitable fluid such as saline or another conductive fluid. The irrigating fluid may cool the electrode 22 of ablation device 20. Irrigated ablation is also known to create deeper lesions that are more likely to be transmural. Transmurality is achieved when the full thickness of the target tissue is ablated. Furthermore, continuous fluid flow may keep the ablation device surface temperature below the threshold for blood coagulation, which may clog the device. Use of irrigating fluid may therefore reduce the need to remove a clogged ablation device for cleaning or replacement. The presence of an ionic fluid layer between electrode 22 and the tissue to be ablated may also ensure that an ionic fluid layer conforming to the tissue contours is created. In one preferred embodiment, saline solution is used. Alternatively, other energy-conducting liquids, such as Ringer's solution, ionic contrast, or even blood, may be used. Diagnostic or therapeutic agents, such as lidocaine, $CA^{++}$ blockers, ionic contrast, or gene therapy agents may also be delivered before, with or after the delivery of the irrigating fluid. Irrigation source 40 may be any suitable source of irrigation fluid such as, for example, a standard irrigation pump (not shown). This pump may also be connected to power source 30 or may have its own source of power. Preferably, device 20 also includes a conduit 38 for delivering irrigation to the ablation site from irrigation source 40.

Figure 2:
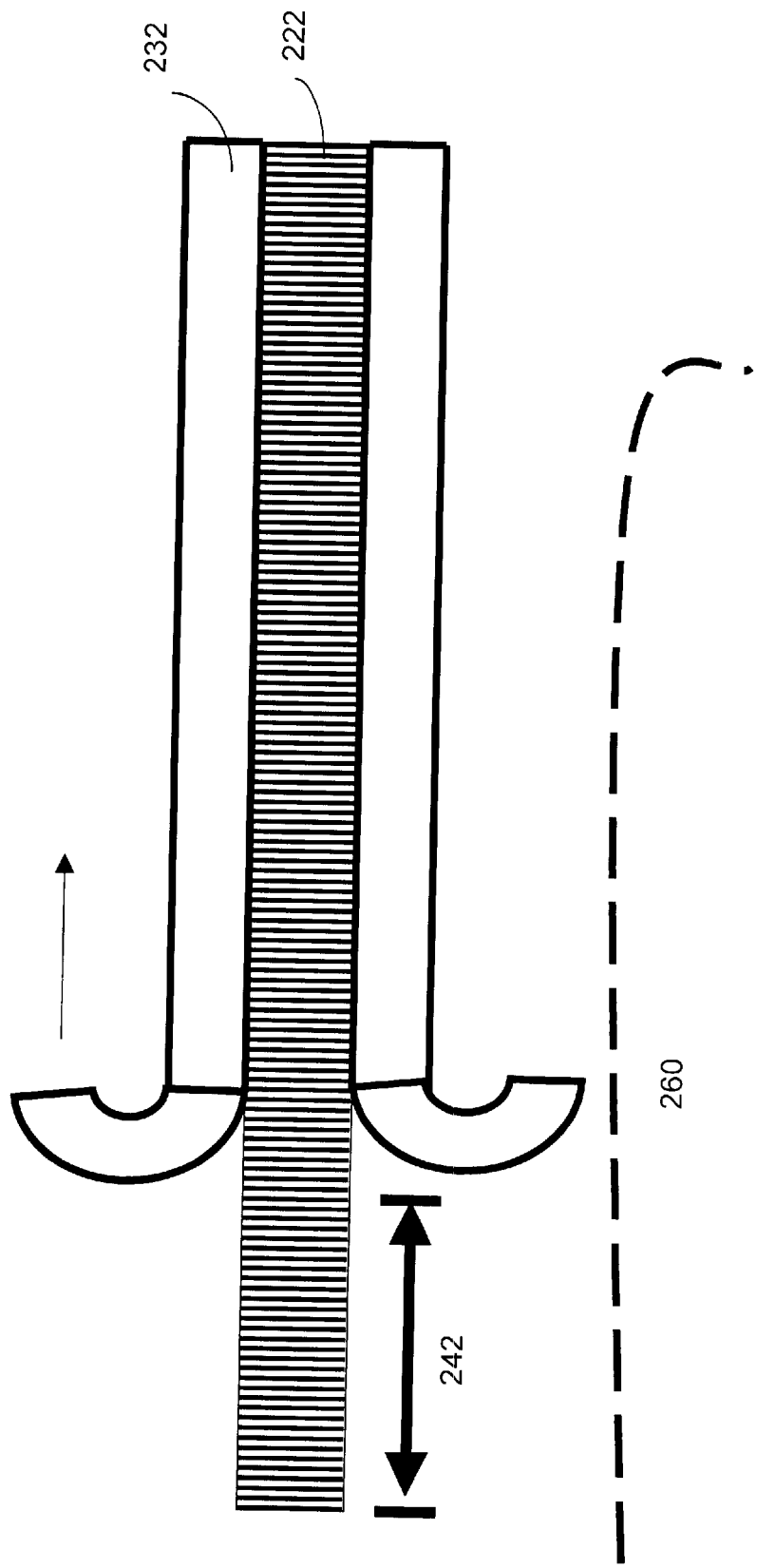
FIG. 2 is a longitudinal schematic view of a variable length ablation electrode in accordance with the present invention.

FIG. 2 shows a schematic representation of one embodiment of a variable length electrode in accordance with the present invention. Electrode 222 may be covered with an insulating material 232. Prior to ablation, insulating material 232 may be removed, for example, by rolling back towards a proximal end of electrode 222. As insulating material 232 is rolled back, ablating surface 242 of electrode 222 may be revealed. The ablating surface may be applied against a surface of tissue 260. The length of ablating surface 242 may vary, depending on the amount of insulating material 232 that is uncovered. Insulating material 232 is preferably a material that insulates the unexposed area of the electrode 222. Such an insulating material may be, for example, silicone or polyurethane. The exposed ablation surface 242 may be conductive and irrigated. However, the section of electrode 222 covered by insulating material 232 may be non-conductive. Furthermore, the section of electrode 222 covered by insulating material 232 may be formed of a material that does not allow irrigating fluid to flow through. Since the irrigating fluid does not flow through the insulated end, a saline bridge as described above may not form. Additionally, the insulating material may direct all energy so that it is delivered to the exposed portion 242 of electrode 222. Additionally, the insulating material may direct all irrigating fluid so that it is delivered to the exposed portion 242 of electrode 222. The irrigation fluid may flow within the insulating material 232 but may not flow through the material 232. Therefore, the unexposed, insulated portion of tool 20 may not be irrigated. The irrigating fluid may thereby delivered only to the desired, exposed portion 242 of electrode 222.

Insulating material 232 may then be returned to its original state to cover exposed surface 242. The same electrode 222 may then be used to ablate a shorter surface. Alternatively, insulating material may be a tip, which may be removed completely. A new insulating material may then be placed over electrode. These tips of insulating material 232 may be of variable length.

Figure 3:
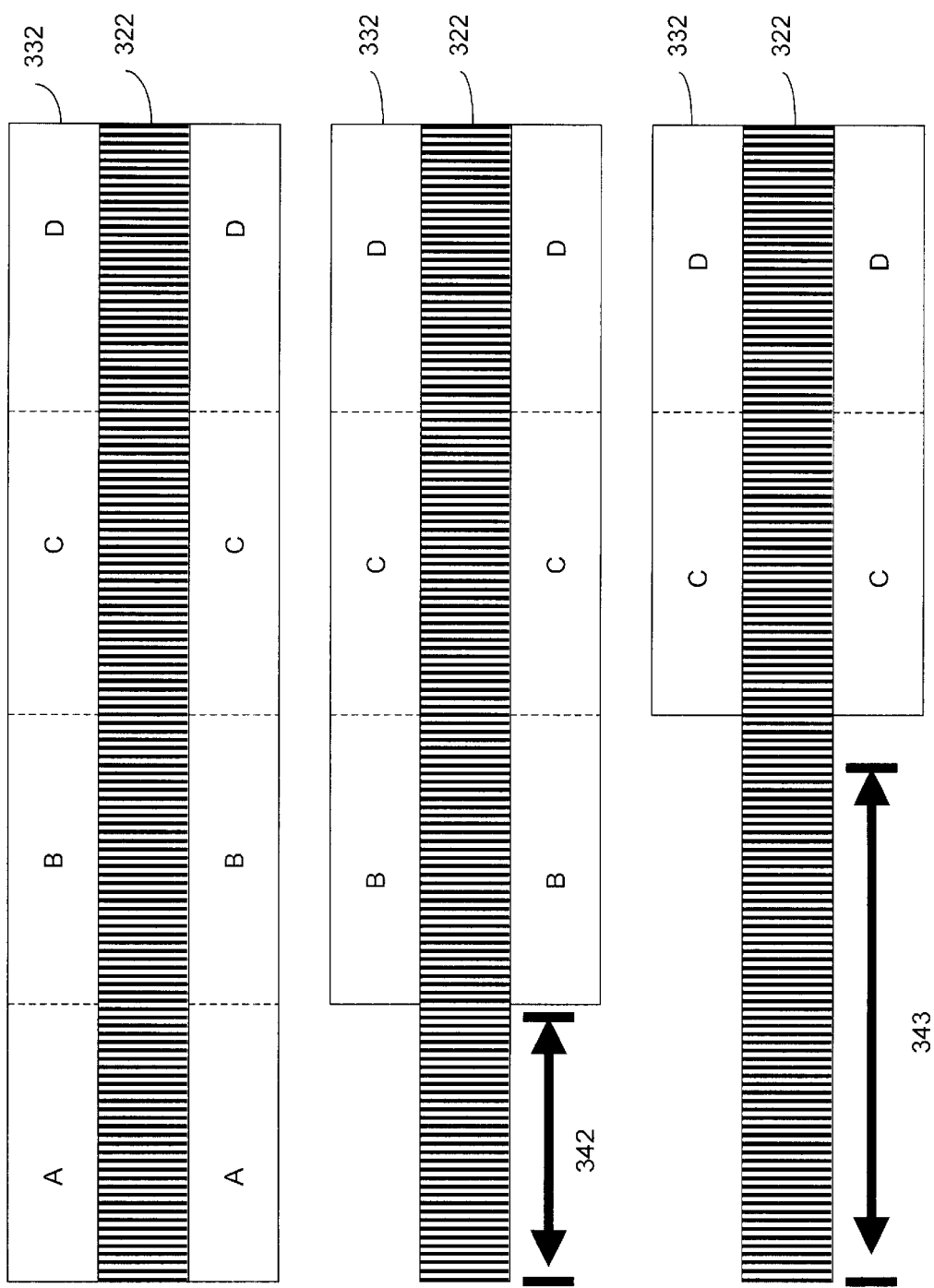
FIG. 3 is a longitudinal schematic view of a second embodiment of a variable length ablation electrode in accordance with the present invention.

FIG. 3 shows a schematic longitudinal representation of another embodiment of the variable length electrode of the present invention. In this embodiment, insulating material 332 is perforated. In use, a user may remove insulating material 332 from segment A, thereby exposing ablation surface 342 as shown. If the user desires, a longer ablation surface in order to create a longer lesion, he may remove additional insulating material 332 from segment B. This results in longer ablation surface 343 as shown. Preferably insulating material that is removed may be disposable.

Figure 4:
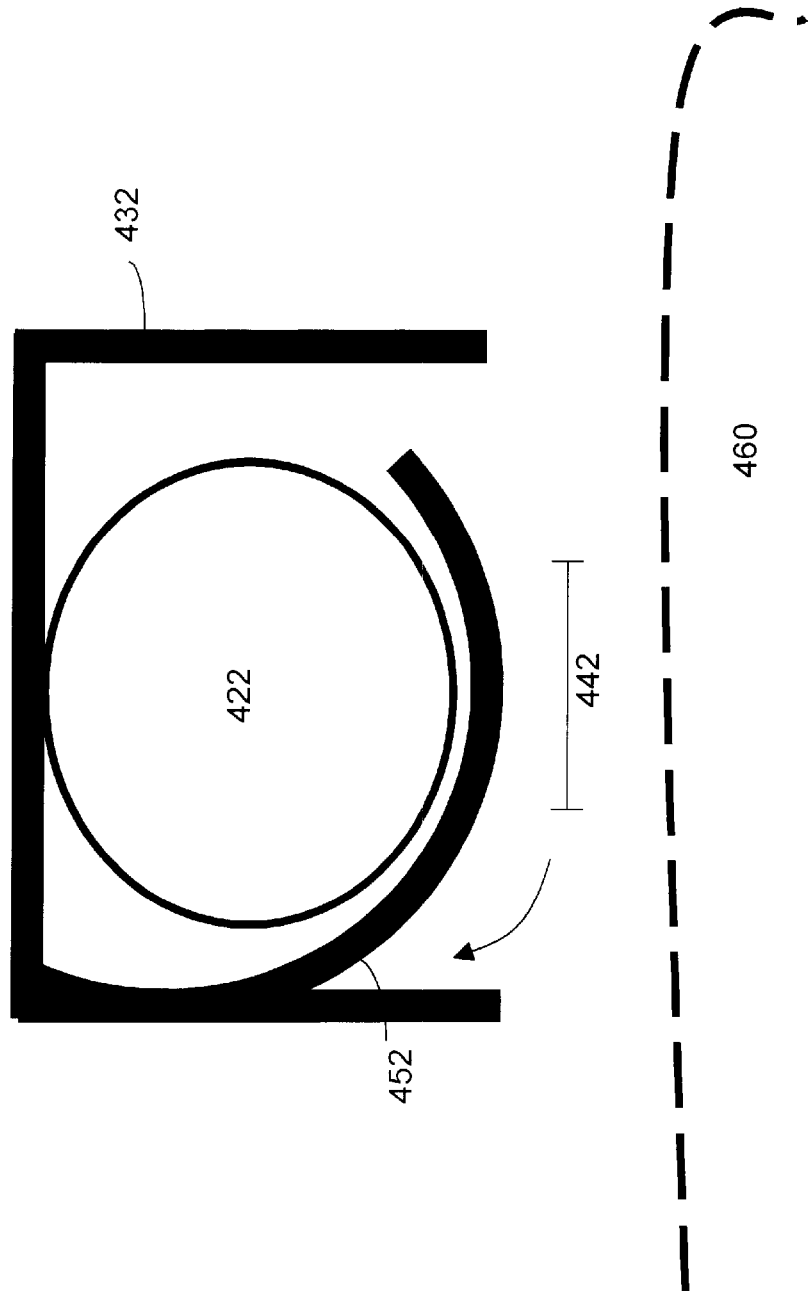
FIG. 4 is a schematic view of a cross-section of a third embodiment of a variable length ablation electrode in accordance with the present invention.

FIG. 4 shows a cross-section view of another embodiment of the variable length electrode of the present invention. In this embodiment, electrode 422 may be covered by insulating material 432 and a rotating portion of insulating material 452. Portion 432 of the insulating material may cover most of the electrode 422. Electrode 422 may remain covered by portion 432 of the insulating material along the length of the electrode. Meanwhile, portion 452 of the insulating material may be removable or movable. Preferably, portion 452 may be rotatably removable or movable. In use, portion 452 of the insulating material may be moved to uncover ablating surface 442. For example, portion 452 of the insulating material may be moved in the direction indicated by the arrow to remove the cover. Portion 452 may be moved to expose ablating surface 442 of electrode 422 along the entire length of electrode 422. Alternatively, portion 452 of insulating material may be moved to uncover ablation surface 442 only along a given portion of electrode 422. Ablating surface 442 may be used to ablate a surface of tissue 460.

Figure 5:
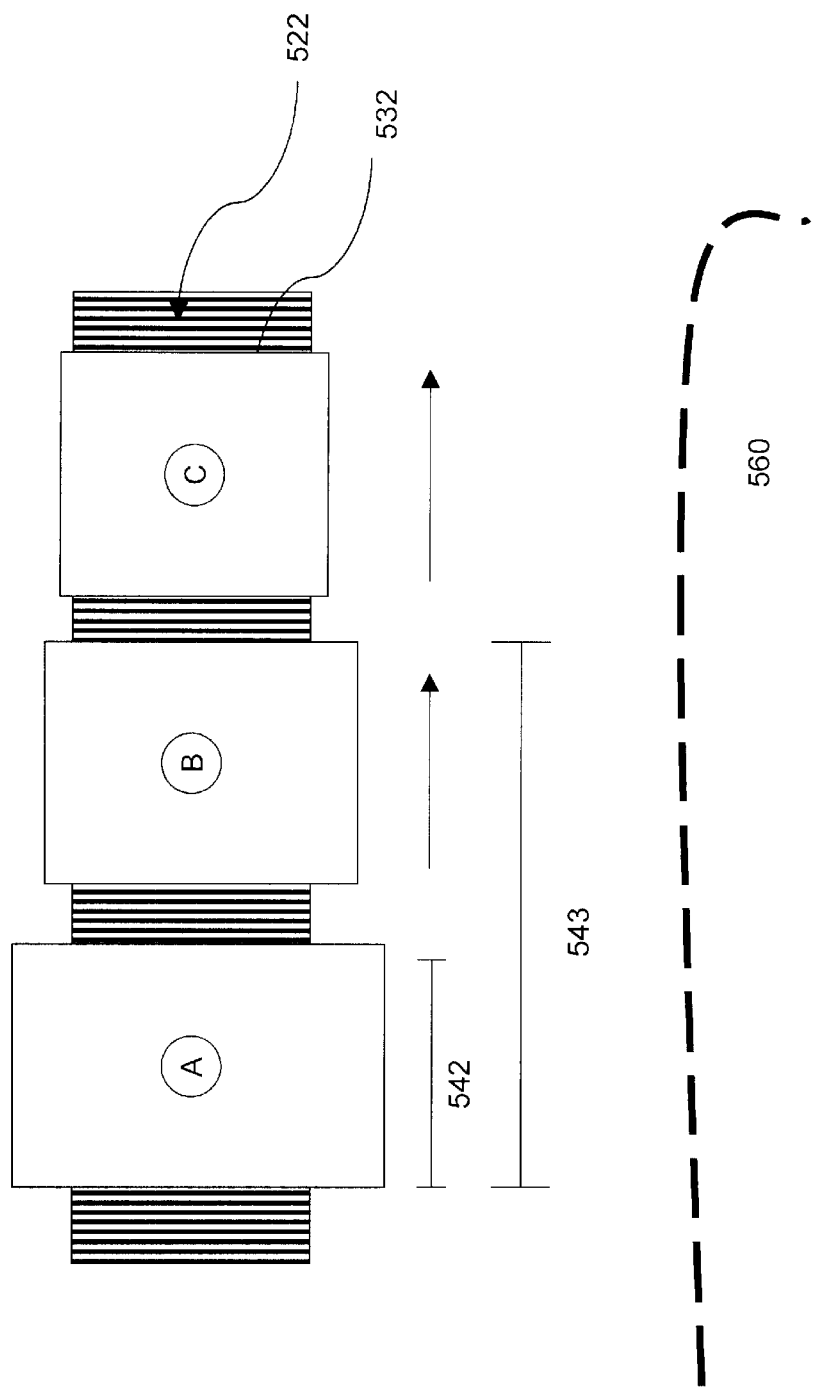
FIG. 5 is a longitudinal schematic view of a fourth embodiment of a variable length ablation electrode in accordance with the present invention.

FIG. 5 shows a longitudinal schematic view of the variable length electrode of the present invention. In use, the insulating material 532 shown in FIG. 5 may be formed as a series of panels that cover electrode 522. For example, three panels, A, B, and C are shown in FIG. 5. Panel A of insulating material 532 may be moved to fit over panel B of insulating material 532. Panel A may be moved, for example, in the direction indicated by the arrows. This may expose ablation surface 542 which may have originally been covered by panel A. If the user desires a longer length electrode to create, for example, a longer lesion, the user may slide panel B over panel C and panel A over panel B to expose an even longer ablation surface 543. Ablating surface 542, 543 may be used to ablate a surface of tissue 560.

In the embodiments shown in FIGS. 1–5, the conductive element may preferably be a coil or spring. Alternatively, the conductive element may be metallic rod with a lumen machined into its axis, a wire braid, a wire mesh or another suitable type of electrode.

Figure 6:
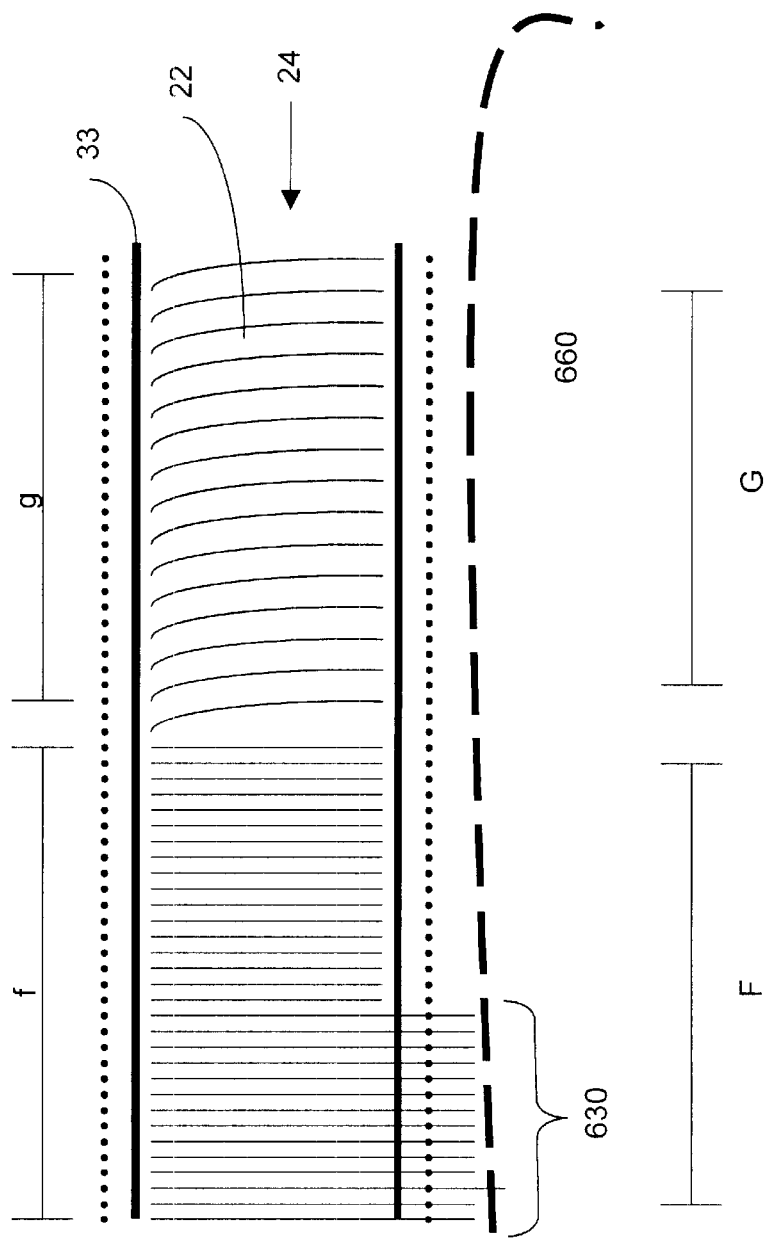
FIG. 6 is a longitudinal schematic view of a fifth embodiment of a variable length ablation electrode in accordance with the present invention.

FIG. 6 shows a longitudinal schematic view of a conductive element 22 in accordance with the present invention. Preferably, the coil or spring may be made of a conductive material such as, for example, metal. This coil may have a lumen 24. Irrigating fluid may be flowed into the lumen 24 of coil 22. For example, irrigating fluid may be pumped from irrigation source 40. As the fluid is pumped from irrigation source 40, the fluid may weep evenly along the length of the coil, thus delivering fluid to the ablation site. A support member 33 may also be incorporated into or adjacent conductive element 22. Preferably support member 33 provides conductive element 22 with additional structural rigidity. The support member 33 may be, for example, a slotted metal tube. The support member may also be made from materials, such as, for example, Nitinol or other superelastic materials, which may allow support and some malleability.

Slotted tube 33 may be formed of a slightly smaller diameter than coil 22. In this case, a portion of coil 22 may protrude through the slot of tube 33 as shown at 630. This protruding of coil 22 may occur along the length of electrode 22. Alternatively, this protruding may occur at a given area of electrode 22. This protrusion may help coil 22 conform to the surface of tissue 660 to be ablated.

Preferably, the pitch or tightness of the coil of conductive element 22 may determine the current density of the conductive element 22. Increasing the pitch of the coil (i.e. winding the coil less tightly) may decrease the current density of the conductive element. Decreasing the pitch may increase the current density of conductive element 22.

Preferably, the pitch or tightness of the coil of conductive element 22 may determine the flow rate of the irrigation fluid through the conductive element 22. Increasing the pitch of the coil (i.e. winding the coil less tightly) may increase the flow rate of irrigation fluid through conductive element 22. Decreasing the pitch may decrease the flow rate of irrigation fluid through conductive element 22.

As seen in the embodiment of FIG. 6, the coil 22 may be a double coaxial, reverse-wound spring. This embodiment, for example, provides an increased resistance to fluid flow and nets a more even distribution along the length of the coil. Therefore, by varying the pitch of a conductive coil 22, characteristics of the lesion created along the length of the electrode may also be varied. Thus if a surgeon were to desire a shallower lesion at section F than at section G, he may use a variable pitch electrode as shown in FIG. 6. The decreased pitch at section f of electrode 22 may result in a lower rate of irrigation flow. This may create a shallower lesion at section F of the tissue. The increased pitch at section g of electrode 22 may result in a higher rate of irrigation flow. This may create a deeper lesion at section G of the tissue.

Figure 7:
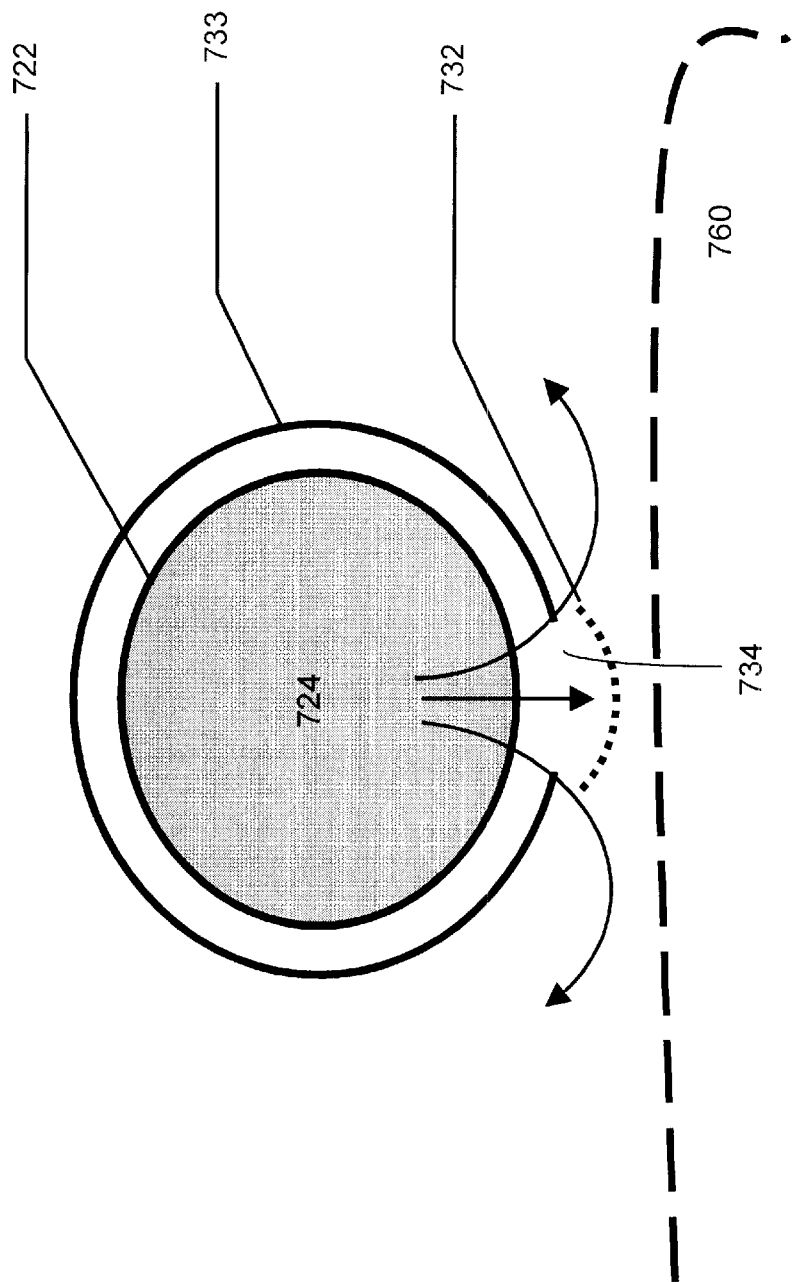
FIG. 7 is a schematic view of a cross-section of one embodiment of an ablation electrode in accordance with the present invention.

FIG. 7 shows a schematic view of a cross-section of a variable length electrode in accordance with the present invention. Conductive element 622 may be for example a double wound coil or spring as described above. Irrigating fluid may be flowed through the lumen 724 of electrode 722. Support element 733 may be for example a slotted tube. Such a slotted tube 733 may be any suitable material that may provide additional structural integrity to conductive element 722. The slotted tube 733 has an opening or slot 734. Preferably this opening 734 may run the length of an entire conductive element 722. This opening 734 may also run the length of an exposed section of a conductive element 722 which may be exposed in a manner as described in the above embodiments. This opening 734 may preferably face a surface of the tissue 760 to be ablated. As shown in FIG. 7, insulating material 732 may cover a portion of conductive element 760 rather than covering the entire conductive element 722. Insulating material 732 may be for example a microporous non-conductive component. Such a microporous non-conductive component may be manufactured from a material such as silicone, PTFE, Dacron fabric or solvent-precipitated polyurethane. Preferably, the pores in the microporous non-conductive component may be large enough to allow the free flow of irrigating fluid but small enough so as not to become clogged with protein or other detritus from the tissue to be irrigated. Irrigating fluid may flow from the lumen 724 of conductive element 722 in the manner indicated by the arrows.

Figure 8:
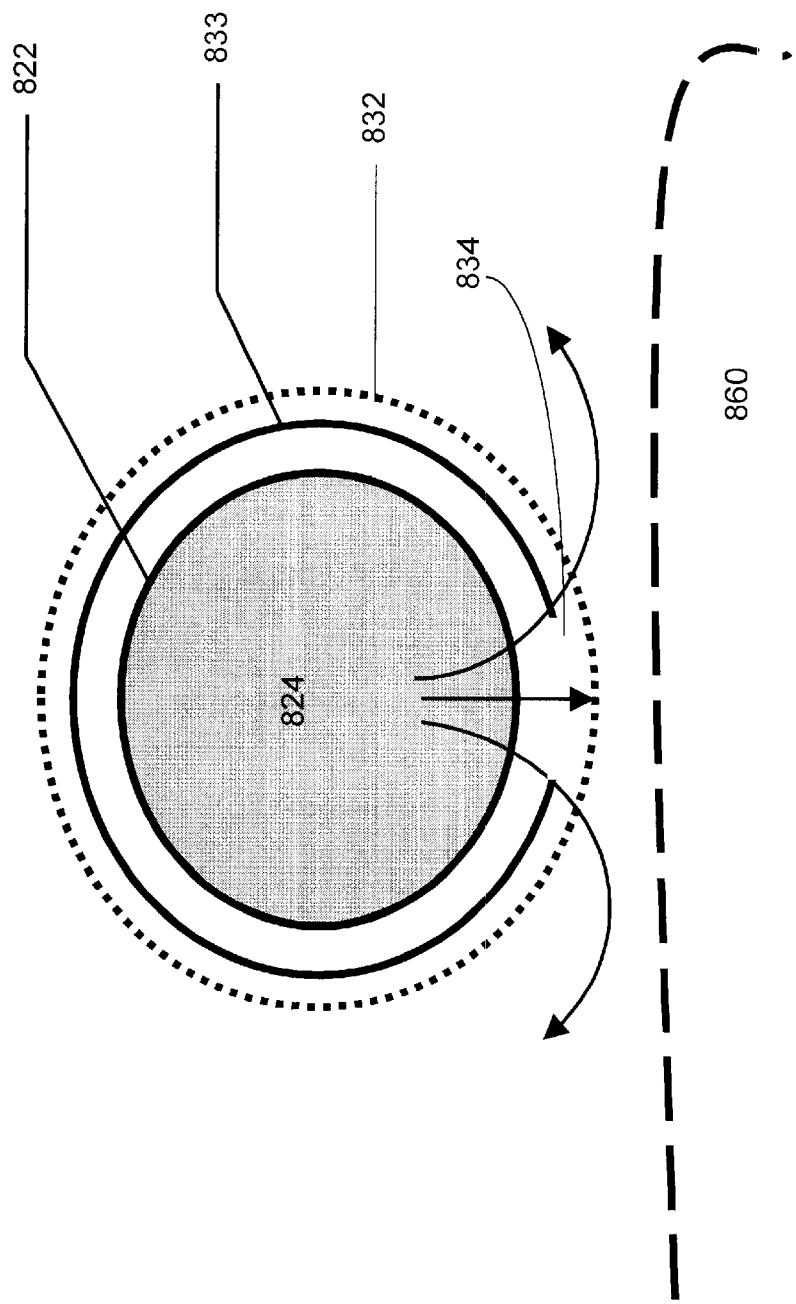
FIG. 8 is a schematic view of a cross-section of another embodiment of an ablation electrode in accordance with the present invention.

FIG. 8 shows a schematic view of a cross-section of a second embodiment of a variable length electrode in accordance with the present invention. Conductive element 822 may be for example a double wound coil or spring as described above. Irrigating fluid may be flowed through the lumen 824 of electrode 822. Support element 833 may be for example a slotted tube. Such a slotted tube 833 may be any suitable material that may provide additional structural integrity to conductive element 822. The slotted tube 833 has an opening or slot 834. Preferably this opening 834 may run the length of an entire conductive element 822. This opening 834 may also run the length of an exposed section of a conductive element 822 which has been exposed in a manner as described in the above embodiments. This opening 834 may preferably face a surface of the tissue 860 to be ablated. As shown in FIG. 8, insulating material 832 may cover all of conductive element 822. Insulating material 832 may also cover slotted tube 833. Insulating material 832 may be for example a microporous non-conductive component. Such a microporous non-conductive component may be manufactured from a material such as silicone, PTFE, Dacron fabric or solvent-precipitated polyurethane. Preferably, the pores in the microporous non-conductive component may be large enough to allow the free flow of irrigating fluid but small enough so as not to become clogged with protein or other detritus from the tissue to be irrigated. Irrigating fluid may flow from the lumen 824 of conductive element 822 in the manner indicated by the arrows.

Figure 9:
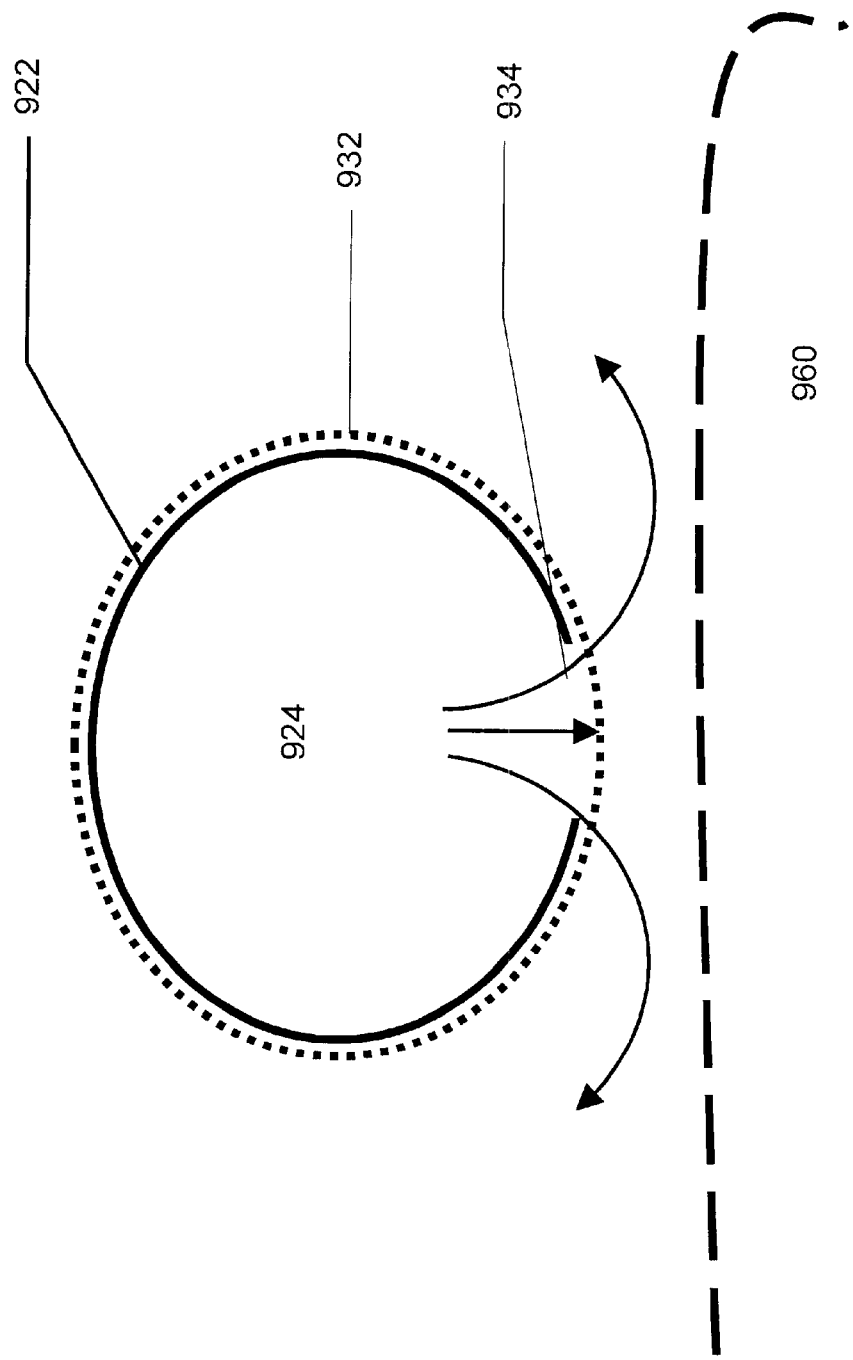
FIG. 9 is a schematic view of a cross-section of another embodiment of an ablation electrode in accordance with the present invention.

FIG. 9 shows a schematic view of a cross-section of a third embodiment of a variable length electrode in accordance with the present invention. Conductive element 922 may be a slotted tube that also serves as a support element. Irrigating fluid may be flowed through the lumen 924 of electrode 922. The slotted tube 922 has an opening or slot 934. Preferably this opening 934 may run the length of an entire conductive element 922. This opening 934 may also run the length of an exposed section of a conductive element 922 which may be exposed in a manner as described in the above embodiments. This opening 934 may preferably face a surface of the tissue 960 to be ablated. As shown in FIG. 9, insulating material 932 may cover all of conductive element 922. Insulating material 932 may be for example a microporous non-conductive component. Such a microporous non-conductive component may be manufactured from a material such as silicone, PTFE, Dacron fabric or solvent-precipitated polyurethane. Preferably, the pores in the microporous non-conductive component may be large enough to allow the free flow of irrigating fluid but small enough so as not to become clogged with protein or other detritus from the tissue to be irrigated. Irrigating fluid may flow from the lumen 924 of conductive element 922 in the manner indicated by the arrows.

Figure 10:
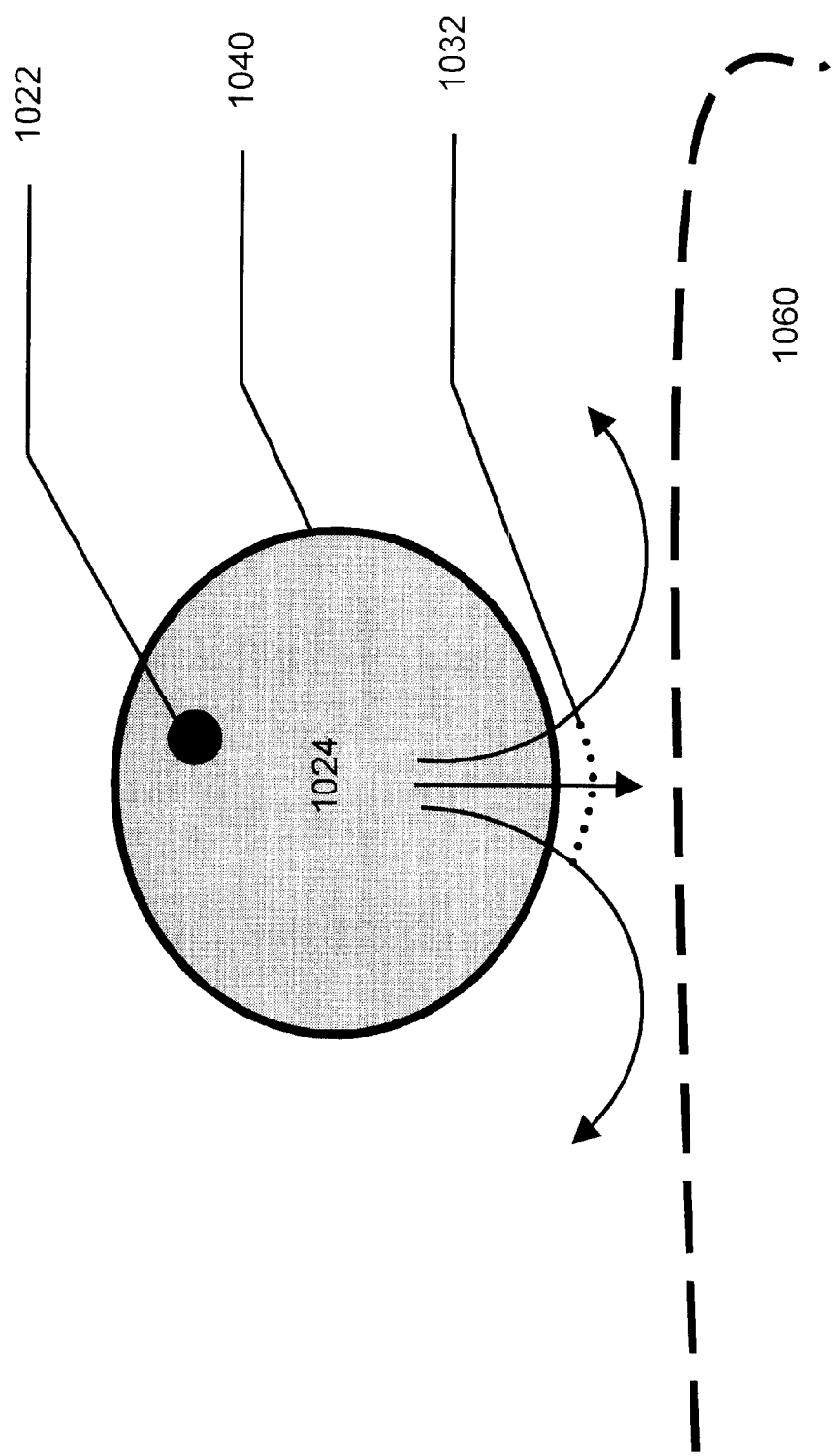
FIG. 10 is a schematic view of a cross-section of another embodiment of an ablation electrode in accordance with the present invention.

FIG. 10 shows a schematic view of a cross-section of a fourth embodiment of a variable length electrode in accordance with the present invention. Conductive element 1022 may be, for example a conductive wire located in a non-porous tube 1040. Irrigating fluid may be flowed through the lumen 1024 of tube 1040. The non-porous tube 1040 may have a segment of insulating material 1032. Preferably this segment 1032 may run the length of an entire conductive element 1022. This segment 1032 may also run the length of an exposed section of a conductive element 1022 which has been exposed in a manner as described in the above embodiments. This segment 1032 may preferably face a surface of the tissue 1060 to be ablated. Insulating material segment 1032 may be for example a microporous non-conductive component. Such a microporous non-conductive component may be manufactured from a material such as silicone, PTFE, Dacron fabric or solvent-precipitated polyurethane. Preferably, the pores in the microporous non-conductive component may be large enough to allow the free flow of irrigating fluid but small enough so as not to become clogged with protein or other detritus from the tissue to be irrigated. Irrigating fluid may flow from the lumen 1024 of non-porous tube 1040 in the manner indicated by the arrows.

Figure 11:
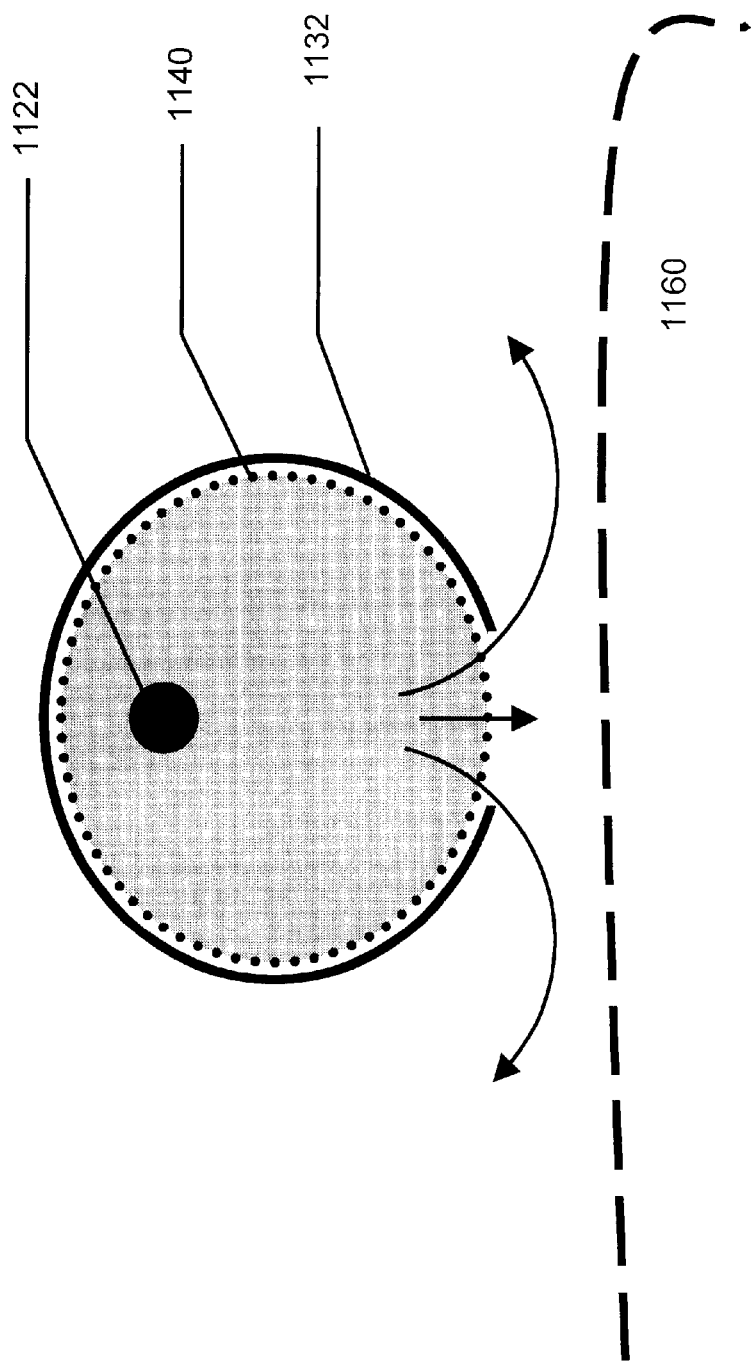
FIG. 11 is a schematic view of a cross-section of another embodiment of an ablation electrode in accordance with the present invention.

FIG. 11 shows a schematic view of a cross-section of a fifth embodiment of a variable length electrode in accordance with the present invention. Conductive element 1122 may be, for example a conductive wire located in a non-porous tube 1140. Irrigating fluid may be flowed through the lumen 1124 of tube 1140. The non-porous tube 1140 may have a rigid segment 1132 of microporous non-conductive material. Preferably this segment 1132 may run the length of an entire conductive element 1122. This segment 1132 may also run the length of an exposed section of a conductive element 1122 which has been exposed in a manner as described in the above embodiments. This segment 1132 may preferably face a surface of the tissue 1160 to be ablated. Rigid segment 1132 may be, for example, a microporous non-conductive component that is rigid. Such a microporous non-conductive component may be manufactured from a material such as rod stock. Preferably, the pores in the microporous non-conductive component may be large enough to allow the free flow of irrigating fluid but small enough so as not to become clogged with protein or other detritus from the tissue to be irrigated. Irrigating fluid may flow from the lumen 1124 of non-porous tube 1140 in the manner indicated by the arrows.

Figure 12:
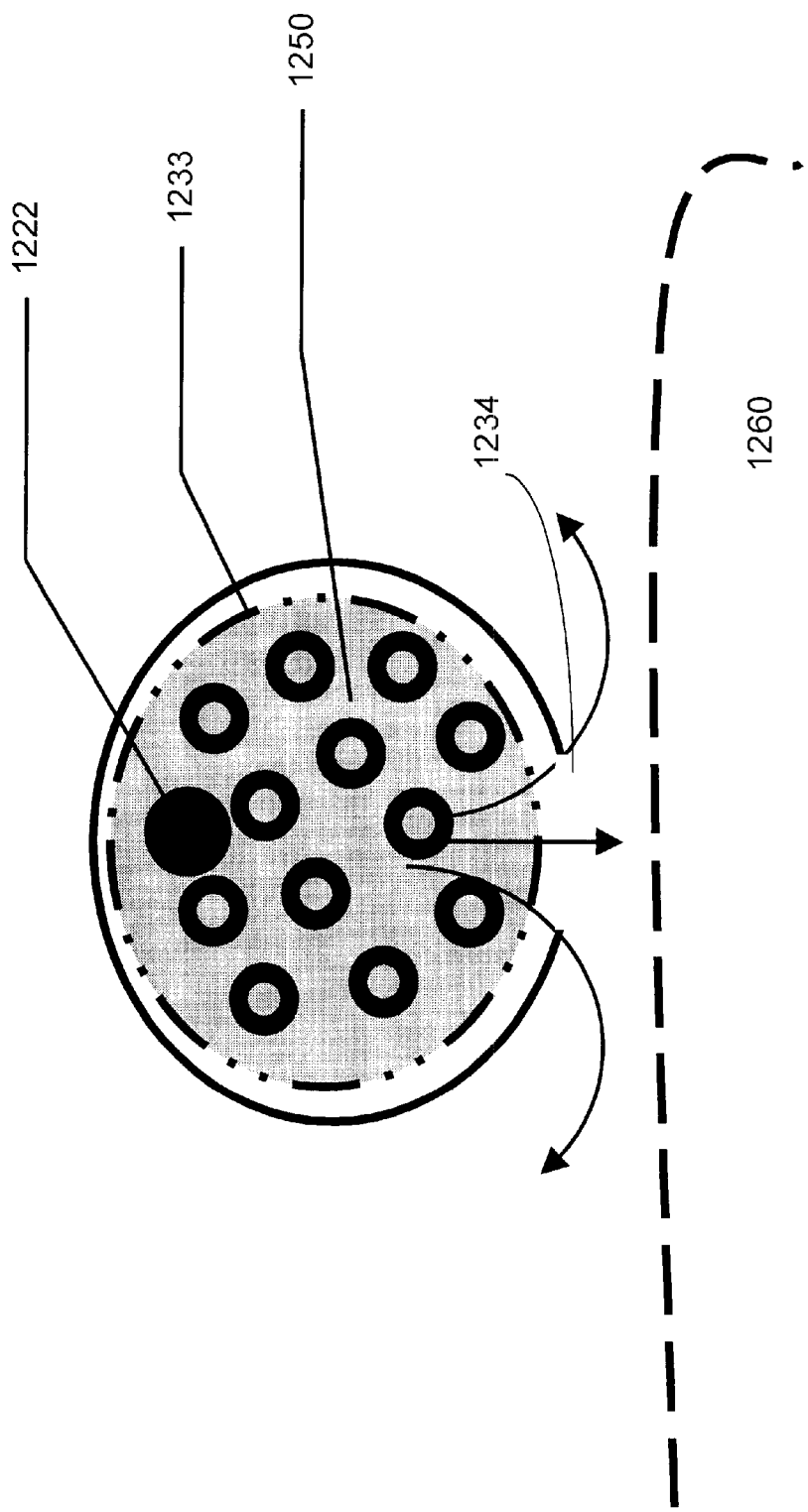
FIG. 12 is a schematic view of a cross-section of another embodiment of an ablation electrode in accordance with the present invention.

FIG. 12 shows a schematic view of a cross-section of a sixth embodiment of a variable length electrode in accordance with the present invention. Conductive element 1222 may be, for example a conductive wire located in a non-porous slotted tube 1233. Such a slotted tube 1233 may be any suitable material that may provide additional structural integrity to conductive element 1222. The slotted tube 1233 has an opening or slot 1234. Preferably this opening 1234 may run the length of an entire conductive element 1222. This opening 1234 may also run the length of an exposed section of a conductive element 1222 which has been exposed in a manner as described in the above embodiments. This opening 1234 may preferably face a surface of the tissue 1260 to be ablated. The lumen 1224 of tube 1233 may be filled with a material 1250 that exudes fluid such as, for example, a hydrogel. Irrigating fluid may be flowed through the hydrogel 1250 as described above. Alternatively, hydrogel 1250 may be saturated with irrigating fluid. When hydrogel 1250 contacts tissue 1260, gel 1250 may exude sufficient irrigating fluid. Tube 1233 may be for example a microporous non-conductive component that is rigid. Such a microporous non-conductive component may be manufactured from a material such as rod stock. Preferably, the pores in the microporous non-conductive component may be large enough to allow the free flow of irrigating fluid but small enough so as not to become clogged with protein or other detritus from the tissue to be irrigated. Irrigating fluid may flow from the lumen 1224 of nonporous tube 1240 in the manner indicated by the arrows.

It is contemplated that the electrodes of the present invention may be used in a variety of ablation systems such as those available from Medtronic, Inc., Minneapolis, USA. It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

We claim:

1. A device for ablating organic tissue comprising:
    a conductive element;
    a fluid component in communication with the conductive element;
    an interface of non-conductive, microporous material positioned adjacent the tissue to allow the fluid to pass through the interface and contact the tissue; and
    a hemostat tool, wherein the conductive element is placed adjacent at least one jaw of the tool.

2. The device of claim 1, wherein the conductive element is a metallic coil with a lumen.

3. The device of claim 1, wherein the conductive element is a spring with a lumen.

4. The device of claim 1, wherein the interface has a length, the length being variable.

5. The device of claim 1, wherein a portion of the interface may be removed to expose the conductive element.

6. The device of claim 1, wherein the interface comprises openings that may be slidably opened.

7. The device of claim 1, wherein the interface lies between the conductive element and the surface of the tissue.

8. The device of claim 1, wherein the interface encircles the conductive element and the fluid component.

9. The device of claim 1, wherein the conductive element is a wire, the wire located within the fluid component.

10. The device of claim 1 further comprising:
    a support element in communication with the conductive element.

11. The device of claim 10, wherein the support element is a slotted tube.

12. The device of claim 1, wherein the conductive element is a slotted tube.

13. The device of claim 1, wherein the non-conductive interface is rigid.

14. The device of claim 1 wherein the non-conductive, microporous material is selected from silicone, PTFE, Dacron, and polyurethane.

15. A device for creating ablations of variable length, comprising:
- a conductive element having a channel formed therein;
- the channel operatively adapted to receive irrigating fluid; and
- a removable non-conductive interface in communication with the conductive element; and
- a maneuvering mechanism operably attached to the conductive element, wherein the maneuvering mechanism is a hemostat tool.

16. The device of claim 15 further comprising:
- a support element in communication with the conductive element.

17. The device of claim 15, wherein the support element is a slotted tube.

18. The device of claim 15, wherein the conductive element is a slotted tube.

19. A device for creating ablations of variable length, comprising:
- a non-porous tube operatively adapted to receive irrigating fluid therein;
- a conductive element in communication with the tube;
- a removable non-conductive interface in communication with the conductive element; and
- a maneuvering mechanism operably attached to the conductive element, wherein the maneuvering mechanism is a hemostat tool.

20. The device of claim 19, wherein the non-conductive interface is rigid.

21. The device of claim 19 further comprising:
- a maneuvering mechanism operably attached to the conductive element.

22. A device for creating ablations of variable length, comprising:
- a non-porous tube operatively adapted to receive a hydrogel;
- a conductive element in communication with the tube;
- a removable non-conductive interface in communication with the conductive element; and
- a maneuvering mechanism operably attached to the conductive element, wherein the maneuvering mechanism is a hemostat tool.

23. The device of claim 22, wherein the tube is slotted.

24. A device for ablating organic tissue, comprising:
- a conductive element;
- a fluid component in communication with the conductive element; and
- a nonconductive interface positioned adjacent the tissue and having openings therein to allow the fluid to pass through the interface and contact the tissue, wherein a portion of the interface may be removed to expose the conductive element.

25. The device of claim 24, wherein the conductive element is a metallic coil with a lumen.

26. The device of claim 24, wherein the conductive element is a spring with a lumen.

27. The device of claim 24, wherein the conductive element has a conductive element diameter and the interface has an interface diameter, the conductive element diameter being greater than the interface diameter.

28. The device of claim 24, wherein the interface has a length, the length being variable.

29. The device of claim 24, wherein the interface is micro-porous.

30. The device of claim 24, wherein the interface is perforated.

31. The device of claim 24, wherein the interface may be rotatably opened.

32. The device of claim 24, wherein the interface comprises openings that may be slidably opened.

33. The device of claim 24, wherein the interface is from the group consisting of: silicones, PTFE, Dacron fabrics, polyurethane, polymeric coatings, polyester fabrics, hydrogels and a gel.

34. The device of claim 24, wherein the interface lies between the conductive element and the surface of the tissue.

35. The device of claim 24, wherein the interface encircles the conductive element and the fluid component.

36. The device of claim 24, wherein the conductive element is a wire, the wire located within the fluid component.

37. The device of claim 24, further comprising:
- means for flowing the fluid component through the interface.

38. The device of claim 24, further comprising:
- an infusion pump in communication with the fluid component for flowing the fluid component through the interface.

39. The device of claim 24, further comprising:
- a maneuvering mechanism operably attached to the conductive element.

40. The device of claim 39, wherein the maneuvering mechanism is a hemostat-type tool.

41. The device of claim 39, wherein the maneuvering mechanism is a catheter.

* * * * *